United States Patent [19]

Bragg

[11] Patent Number: 5,282,855
[45] Date of Patent: Feb. 1, 1994

[54] VAULTED INTRAOCULAR LENS HAVING CURVED SLANTED HAPTIC

[75] Inventor: Joseph A. Bragg, Milton, W. Va.

[73] Assignee: Alcon Surgical, Inc., Fort Worth, Tex.

[21] Appl. No.: 971,021

[22] Filed: Nov. 2, 1992

Related U.S. Application Data

[63] Continuation of Ser. No. 789,376, Nov. 5, 1991, Pat. No. 5,160,345, which is a continuation of Ser. No. 591,226, Oct. 1, 1992, abandoned.

[51] Int. Cl.$^5$ ............................................. A61F 2/16
[52] U.S. Cl. ................................................... 623/6
[58] Field of Search ........................................ 623/6

[56] References Cited

U.S. PATENT DOCUMENTS

| | | | |
|---|---|---|---|
| 4,110,848 | 9/1978 | Jensen | 623/6 |
| 4,363,143 | 12/1982 | Callahan | 623/6 |
| 4,370,760 | 2/1983 | Kelman | 623/6 |
| 4,403,353 | 9/1983 | Tennant | 623/6 |
| 4,409,691 | 10/1983 | Levy | 623/6 |
| 4,418,431 | 12/1983 | Feaster | 623/6 |
| 4,437,194 | 3/1984 | Hahs | 623/6 |
| 4,547,914 | 10/1985 | Castleman | 623/6 |
| 4,575,374 | 3/1986 | Anis | 623/6 |
| 4,585,455 | 4/1986 | Blackmore et al. | 623/6 |
| 4,589,147 | 5/1986 | Nevyas | 623/6 |
| 4,624,670 | 11/1986 | Bechert, II | 623/6 |
| 4,629,460 | 12/1986 | Dyer | 623/6 |
| 4,634,442 | 1/1987 | Link | 623/6 |
| 4,664,666 | 5/1987 | Barrett | 623/6 |
| 4,710,195 | 12/1987 | Giovinazzo | 623/6 |
| 4,734,095 | 3/1988 | Siepser | 623/6 |
| 4,816,032 | 3/1989 | Hetland | 623/6 |
| 4,842,602 | 6/1989 | Nguyen | 623/6 |
| 4,936,850 | 6/1990 | Barrett | 623/6 |

FOREIGN PATENT DOCUMENTS

01759772A1 9/1985 European Pat. Off. .

OTHER PUBLICATIONS

CILCO Lens Description Sheet, published Mar., 1984.

Primary Examiner—Robert C. Shay
Attorney, Agent, or Firm—James Arno; Jeffrey Schira; Christopher Brody

[57] ABSTRACT

An intraocular lens designed for ease of insertion and for minimizing contact with intraocular tissues comprises a lens body having an optical axis, two optical surfaces and a periphery to which is fixed at least one filamentous haptic extending circumferentially and radially from the point of attachment along a curvilinear path in space to a maximum distance from the optical axis. The haptic has a proximal segment adjacent to the attachment point, a medial segment attached to and continuous with the proximal segment and a distal segment attached to and continuous with the medial segment. At least a part of the distal segment lies at the maximum distance from said optical axis and constitutes the tissue-contacting portion of the haptic. The tissue-contacting element is tangent to a second plane parallel to the first plane and displaced from it along the optical axis, and at least the medial segment of the haptic traverses a path concave toward the first plane and avoiding intersection with the second plane.

7 Claims, 2 Drawing Sheets

VAULTED INTRAOCULAR LENS HAVING CURVED SLANTED HAPTIC

This is a continuation, of application Ser. No. 07/789,376 filed on Nov. 5, 1991, now U.S. Pat. No. 5,160,345 which is a continuation application of Ser. No. 07/591,226 filed on Oct. 1, 1992.

BACKGROUND OF THE INVENTION

1. Field of the invention

This invention relates to intraocular lenses (IOL's) and more particularly to intraocular lenses wherein the optic member of the lens is axially displaced from the supporting points within the eye.

2. Brief description of the prior art

The implantation of an intraocular lens (IOL) to restore vision after the extraction of a cataractous crystalline lens has come to be a common procedure. Such lenses have been implanted in the anterior chamber or posterior chamber of the eye, and a variety of methods have been developed for fixing the lenses in their proper position. The typical intraocular lens comprises a central lens body (often called the "optic") which replaces the original crystalline lens of the eye, and supporting structures (often called "haptics") which are fixed to the optic and extend therefrom so as to support the lens centrally within the eye. The haptics generally comprise structural elements extending radially from the optic so that when in place within the eye they engage the surrounding ocular tissues and provide support for the lens portion. It is common to use haptics which are flexible strands or filaments of biologically inert material which extend radially from the central lens and support it by pressing against the surrounding tissue.

When intraocular lenses are implanted in the anterior chamber of the eye, the haptics commonly contact the anterior chamber angle. When implanted in the posterior chamber, the haptics may be placed either in the residual portion of the lens capsule, if present, or in the ciliary sulcus, immediately behind the iris. In either position of implantation, care must be taken to prevent the lens from contacting the iris and blocking the pupil, for such a blockage will prevent the flow of aqueous humor through the pupil and result in an elevated intraocular pressure. It is also important to prevent the lens from rubbing against the iris. Such rubbing can result in dispersion of the pigment in the iris, which is referred to as pigmentary dispersion syndrome. This syndrome can lead to the formation of translucent sections of the iris, and in turn a condition known as pigmentary glaucoma. Finally, it is additionally important to prevent contact between the lens and the iris in order to avoid the possibility that the lens will be captured by the pupil upon contraction or dilation of the iris, which may result in displacement of the lens, as well as other problems.

In response to the above-cited concerns, the intraocular lens designs of the prior art have included configurations wherein the haptics or supporting loops extend anteriorly from the optical portion of the lens. Such configurations are generally referred to as "vaulted" posterior chamber lenses. When such a "vaulted" lens is implanted, the outer ends of the haptics may be located adjacent to the peripheral iris in the ciliary sulcus, capsular bag or anterior chamber angle, while the lens body is axially displaced away from the pupillary opening of the iris.

Two general styles of vaulted lenses especially adapted for posterior chamber implantation have been developed. In the so-called "step-vaulted" design, the segment of the haptic nearest the optic extends in an angled direction out of the plane of the optic, usually at a relatively large angle, e.g., about 20°, while the distal segment is constructed parallel to the plane of the lens. In this design the outer segment of the haptic runs generally parallel to the plane of the iris, and consequently this segment of the haptic may come into contact with the iris creating a serious potential for injury.

In another type of vaulted IOL the haptic extends from the periphery of the optic at a constant angle to the plane of the optic along its length until it reaches the designed radial distance. This design, commonly referred to as an "angled" form of vaulting, avoids the problem of excessive contact with the iris, but introduces a drawback in the procedure for implantation. It is customary to implant the IOL in the eye after the removal of the cataract by sliding it laterally at a slight angle through the small incision below the cornea, through the iris and into the posterior chamber. It is also customary to fill the cavity caused by the removal of the cataract with a viscoelastic material, e.g., hyaluronic acid, in order to maintain the shape of the cavity from which the crystalline lens was removed and protect the delicate tissues of the eye. However, as the IOL is being moved laterally into the viscoelastic-filled posterior chamber, the angled haptic tends to be deflected by the drag of the viscoelastic material as it is moved therethrough, because the haptic, particularly the leading edge is presented to the viscoelastic face at a relatively high angle of incidence.

Accordingly, a need has continued to exist for a vaulted intraocular lens that avoid both the problem of contact with the iris and that of excessive deflection of the haptic during implantation.

SUMMARY OF THE INVENTION

This goal has now been accomplished by an intraocular lens comprising:

an optic having an optical axis, two surfaces intersecting the optical axis and a periphery surrounding said surfaces, at least a portion of the periphery lying in a first plane perpendicular to the optical axis;

at least one filamentous haptic attached to said optic at a point of attachment on the periphery, the haptic projecting circumferentially and radially from the point of attachment along a curvilinear path in space to a maximum distance from said optical axis;

the haptic having a proximal segment adjacent to the attachment point, a medial segment attached to and continuous with the proximal segment and a distal segment attached to and continuous with the medial segment, at least a part of the distal segment lying at the maximum distance from said optical axis and constituting a tissue-contacting element of the haptic, The tissue-contacting element being tangent to a second plane parallel to the first plane and displaced from it along the optical axis, and at least the medial segment of the haptic traversing a path concave toward the first plane, and avoiding intersection with the second plane.

Accordingly, it is an object of the invention to provide a new, improved type of vaulted intraocular lens.

A further object is to provide a vaulted intraocular lens that minimizes contact of the haptics with the iris.

A further object is to provide a vaulted intraocular lens that minimizes deflection of the haptics during implantation.

A still further object is to provide a vaulted intraocular lens that exhibits better anterior/posterior stability.

Another object is to provide a vaulted intraocular lens that exhibits less posterior deflection.

Other objects of the invention will become apparent from the description of the invention which follows.

DETAILED DESCRIPTION OF THE INVENTION AND PREFERRED EMBODIMENTS

The intraocular lens of this invention addresses the problem of haptic deflection during implantation by arranging for the distal or outermost segment of the haptic, i.e., that segment that leads when the lens is inserted, to be directed parallel to the plane of the lens body, or optic, itself. At the same time, that segment of the haptic immediately following the distal segment as the lens is inserted is gradually curved toward the plane of the lens. Accordingly, when the lens reaches the final implanted position, only the distal segment of the haptic makes contact with the tissue of the eye. In particular, the haptic does not come into contact with the portions of the iris which are located radially closer to the optic axis of the IOL than are the distal segments of the haptic.

Figure 1:
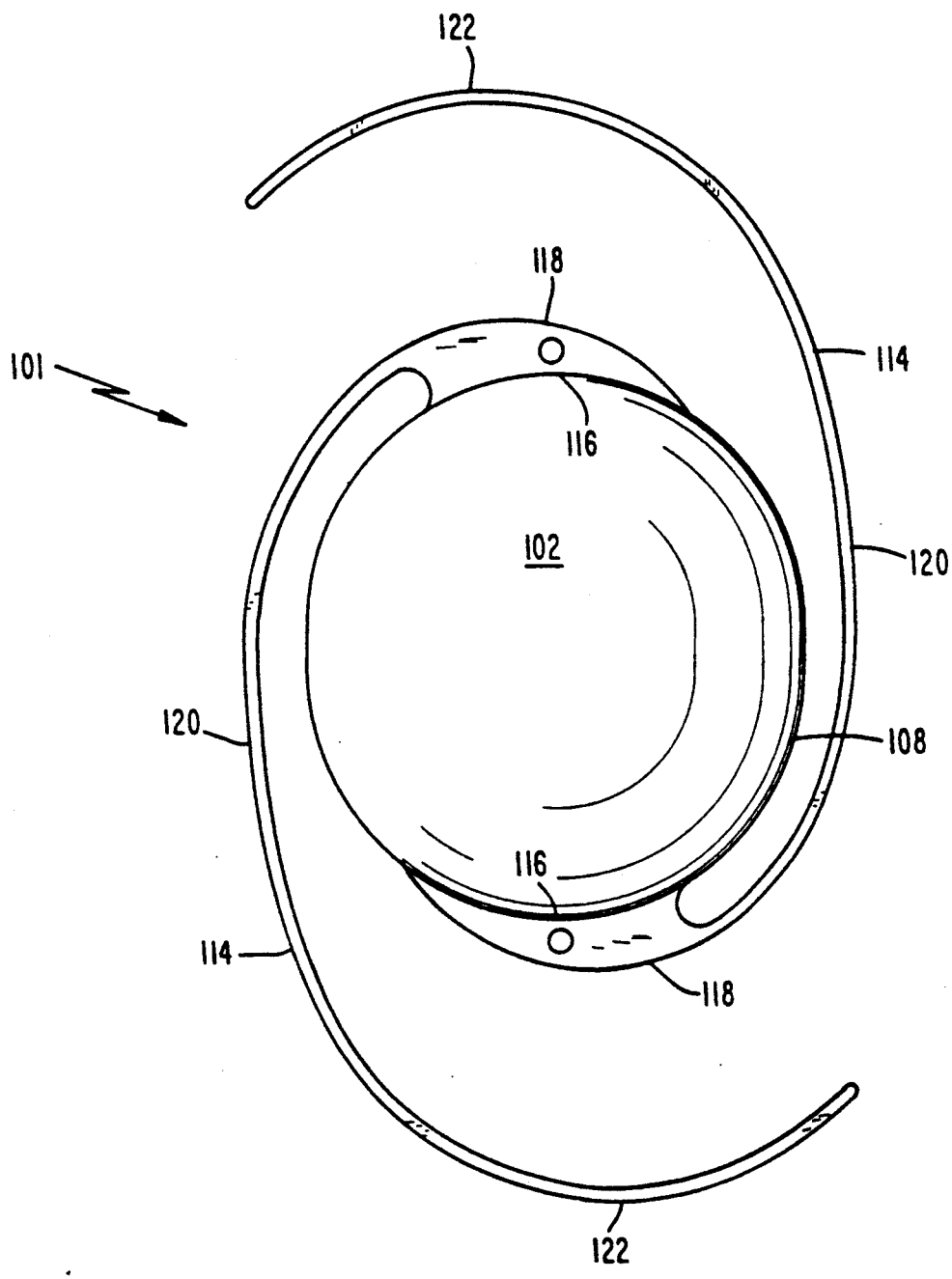
FIG. 1 shows a front elevational view of the intraocular lens of this invention.
Figure 2:
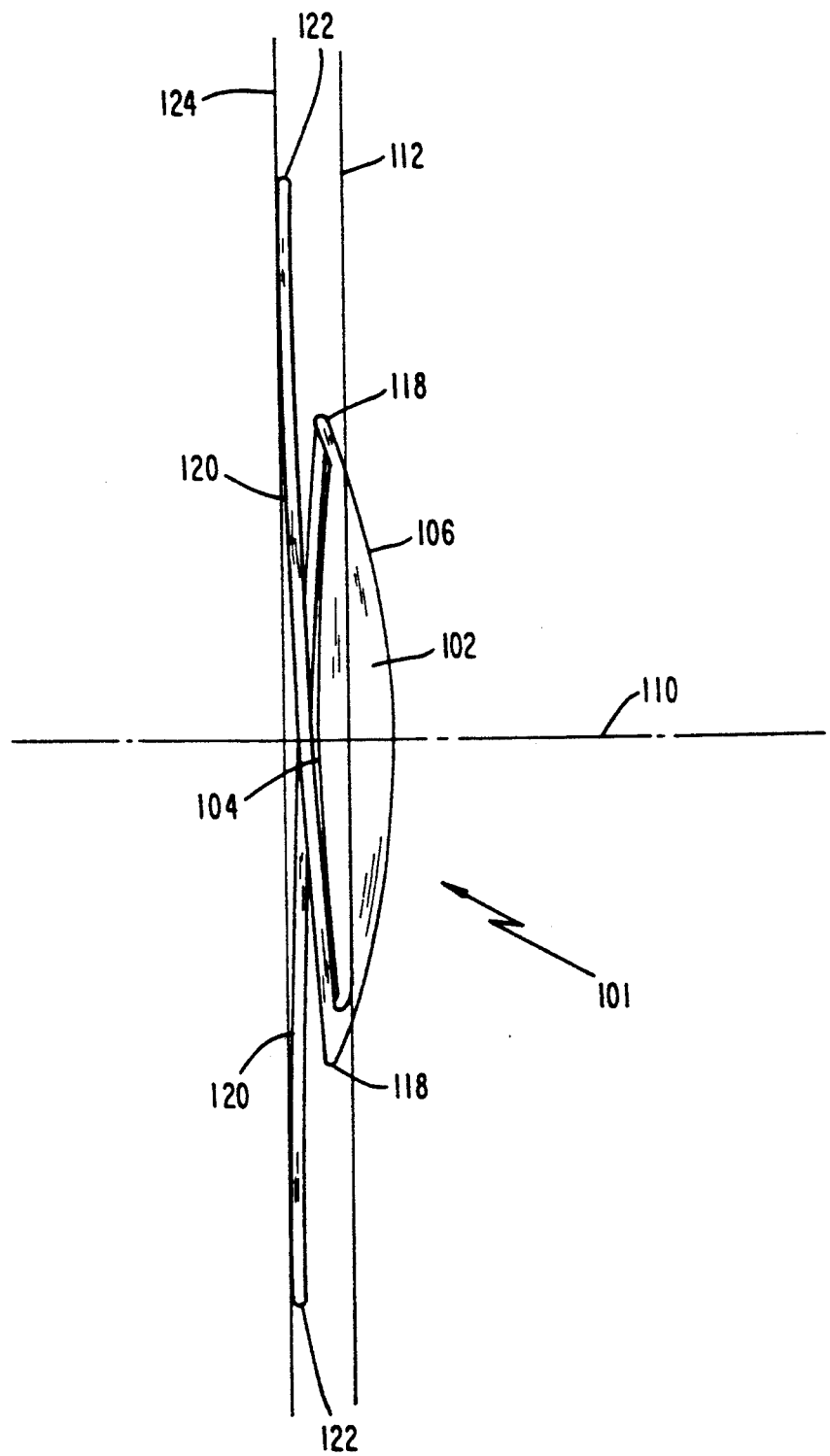
FIG. 2 shows a side elevational view of the intraocular lens of this invention.

Referring to FIGS. 1 and 2, wherein the reference numerals refer to the same elements throughout, the IOL 101 of this invention comprises a central lens body or optic 102 having an optical axis 110 and bounded by a front surface 104 and a rear surface 106, both surfaces intersecting the optical axis 110. Typically the two surfaces will be convex, so that the optic element 102 of the IOL is a biconvex lens. However, a plano-convex design is also possible; even a concavo-convex, or meniscus, lens could be used if appropriate. The lens body may be made of any transparent biologically inert material. A preferred material for the lens body is poly(methyl methacrylate).

The optic 102 is bounded by a periphery 108, which typically is a smooth curve. The periphery may be circular, elliptical or may be a closed curve of any other convenient shape. At least a portion of the periphery 108 lies in a first plane 112 perpendicular to the optical axis. In a preferred embodiment, the entire smooth curve forming the periphery 108 will lie in the first plane 112. At least one haptic 114 is fixed to the optic 102 attached to the periphery 108. Typically, as shown in the illustrated embodiment of the invention, the IOL will have two haptics 114, attached to the periphery 108 of the optic at diametrically opposite attachment locations 116.

The haptics 114 are filamentous structures projecting from the periphery 108 of the optic 102. The haptics have a proximal segment 118, adjacent to the location 116 at which they are fixed to the optic 102, a distal segment 122 that is at a maximum distance from the optical axis 110, and a medial segment 120 joining the proximal and distal segments of the haptic.

The haptics may be made from any suitable material such as poly(methyl methacrylate), polyester, polyamide, polypropylene or the like. It is preferred that both the optic and the haptic be made of the same material, e.g., poly(methyl methacrylate) and be cut from the same blank so that the haptics are an integral part of the IOL.

The haptics 114 project from the attachment location 116 on the periphery 108 of the optic 102 in a generally radially outward and circumferential direction and so that their distance from the optical axis 110 gradually increases from the proximal segment 118 toward the distal segment 122. The distal segment 122 of the haptic 114 lies at the greatest distance from the optical axis 110. It is the distal segment 122 of the haptic 114 that comes into contact with the tissue of the eye and thereby supports the IOL in its central location on the optical axis of the eye. If the capsular bag remains in place in the eye after the crystalline lens has been removed, the distal segment of the haptics may bear against the periphery of the bag and thereby support the lens. Alternatively, particularly if the lens capsule has been removed, the distal segment of the haptic may contact the ciliary sulcus. The distal segment 122 of the haptic 114 may have a smooth curve that contacts the ocular tissue along its entire length as illustrated in the drawings. As another alternative, the distal segment of the haptic may be other than a smooth curve, such that it contacts the ocular tissue at only one point or several points along its length.

The distal segments 122 of the haptics 114 are displaced from the first plane 112 by a distance along the optical axis and are tangent to a second plane 124 perpendicular to the optical axis and displaced from the first plane. The distance between the first and second planes is chosen to provide sufficient clearance between the iris and the surface of the optic 102 closest to the iris to avoid the danger that the optic might come into contact with the iris and block the flow of aqueous humor through the pupil.

At least the medial segments 120 of the haptics 114, are curved so as to be concave toward the first plane 112. The phrase "concave toward the first plane", as used herein, is intended to define a configuration in which the haptic traverses a path in space such that a tangent to that path makes an angle with the plane of the optic, which steadily, i.e., monotonically, decreases as the haptic extends from the point of attachment with the optic to the distal end thereof, at which point it is substantially parallel to the plane of the optic. In the preferred embodiment illustrated, the medial segments 120 and the proximal segments 118 of the haptics 114 curve smoothly from the attachment location 116 to the distal segments 122. This curvature assures that only the distal segments 122 of the haptics 114 will contact the second plane 124 which corresponds to the plane of the iris in the eye. In this way contact of the haptics with the iris is minimized or eliminated, since the haptics contact the ocular tissue only at the distal segments 122. At the same time, the medial segment 120 of the haptic 114 as it approaches the distal segment 122 is directed toward the plane 124 which is perpendicular to the optical axis. This orientation of the outer portions of the haptic provides advantages in the process of implanting the lens into the eye, as explained below.

After the surgeon has removed the crystalline lens from its location behind the iris, he generally fills the cavity with a viscoelastic medium, typically hyaluronic acid, to retain the shape of the cavity during the subsequent implantation procedure. The IOL is then inserted into the cavity by sliding it laterally, i.e., parallel to the plane of the lens 112, at an angle through the pupil and into the posterior chamber. In this procedure, the distal segment 122 of the haptic 114 is the leading edge of the IOL as it is implanted. Because the medial segment 120 of the haptic 114 at its juncture with the distal segment 122 is directed nearly parallel to the second plane 124, the haptic initially experiences little tendency to be deflected. Consequently, there is initially very little force required to move the distal segment 122 of the haptic 114 out of the second plane 124. As the lens is inserted further into the viscoelastic material filling the posterior chamber, the more slanted segments of the haptic 114 come into contact with the viscoelastic material. However, the bending force on the haptic 114 will still be smaller than it would be if the medial segment 120 had a constant angle. Accordingly, the IOL of this invention enjoys the advantage of easier and more trouble-free insertion. At the same time, as pointed out above, the curve of the medial segment 120 of the haptic 114 away from the second plane 124 assures that the haptic will contact the ocular tissues only at its distal segment 122. In particular, the haptic 114 will be less likely to contact the iris than haptics wherein the distal segment is oriented parallel to the iris.

The manufacture of IOL's according to this invention is conventional. The optic may be molded or cut from a blank and the haptics may be subsequently attached. However, as previously indicated, it is preferred that the entire IOL be cut from a single blank of a suitable material, e.g., poly(methyl methacrylate).

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

What is claimed is:

1. An intraocular lens comprising:
    a lens body having an optical axis, two surfaces intersecting said optical axis and a periphery, at least a portion of said periphery lying in a first plane perpendicular to said optical axis;
    at least one filamentous haptic attached to said lens body at a point of attachment on said periphery;
    said at least one haptic having a proximal segment adjacent to said attachment point, a medial segment attached to and continuous with said proximal segment and a distal segment attached to and continuous with said medial segment and having a distal end,
    said at least one haptic projecting radially and circumferentially from said point of attachment along a curvilinear path in an unstressed state in a space adjacent said first plane to a maximum distance from said optical axis, said curvilinear path in said space defined such that a tangent to said curvilinear path makes an angle with said first plane which monotonically decreases as the haptic extends from said point of attachment to said distal segment, said tangent being parallel to said first plane when contacting said distal end;
    said distal end lying at said maximum distance from said optical axis and constituting a tissue contacting element of said at least one haptic,
    said tissue-contacting element contacting a second plane parallel to said first plane and displaced from it along said optical axis, and
    at least said medial segment of said haptic traversing a path concave toward said first plane, and avoiding intersection with said second plane.

2. The intraocular lens of claim 1 wherein said lens body is a biconvex lens.

3. The intraocular lens of claim 1 wherein said lens body is a plano-convex lens.

4. The intraocular lens of claim 1 wherein the at least one filamentous haptic thereof comprises a pair of said haptics which are attached at diametrically opposite points of said periphery, said haptics extending along oppositely disposed paths around the optical axis of the lens.

5. The intraocular lens of claim 1 wherein said distal segment of said at least one haptic is radially outwardly convex.

6. The intraocular lens of claim 1 wherein said medial segment of said at least one haptic extends along a path progressively further from said optical axis.

7. An intraocular lens comprising:
    a lens body having an optical axis, two surfaces intersecting said optical axis and a periphery, at least a portion of said periphery lying in a first plane perpendicular to said axis;
    a pair of filamentous haptics attached to said lens body at diametrically opposite points of attachment on said periphery;
    each of said haptics having a proximal segment adjacent to said attachment point, a medial segment attached to and continuous with said proximal segment and a distal segment attached to and continuous with said medial segment and having a distal end,
    each of said haptics projecting radially and circumferentially from said point of attachment in a direction which is opposite from that of the other one of said pair of haptics, along a curvilinear path in an unstressed state in a space adjacent said first plane to a maximum distance from said optical axis, said curvilinear path in said space defined such that a tangent to said curvilinear path makes an angle with said first plane which monotonically decreases as each haptic extends from each said point of attachment to each said distal segment, said tangent being parallel to said first plane when contacting said distal end;
    said distal ends lying at said maximum distance from said optical axis and constituting a tissue contacting element of each said haptic,
    each said tissue contacting element contacting a second plane parallel to said first plane and displaced from it along said optical axis, and
    at least said medial segment of each said haptic traversing a path which is concave toward said first plane, extends progressively further from said optical axis, and avoids intersection with said second plane.

* * * * *